US 9,250,212 B2

(12) United States Patent
S. et al.

(10) Patent No.: US 9,250,212 B2
(45) Date of Patent: Feb. 2, 2016

(54) AUTOMATIC FIRST ELEMENT SELECTION FOR PHASED ARRAY WELD INSPECTION

(71) Applicant: General Electric Company, Schenectady, NY (US)

(72) Inventors: Anandamurugan S., Bangalore (IN); Sangeetha Mylswamy, Tamilnadu (IN)

(73) Assignee: GENERAL ELECTRIC COMPANY, Shenectady, NY (US)

(*) Notice: Subject to any disclaimer, the term of this patent is extended or adjusted under 35 U.S.C. 154(b) by 340 days.

(21) Appl. No.: 13/873,308

(22) Filed: Apr. 30, 2013

(65) Prior Publication Data

US 2014/0318248 A1    Oct. 30, 2014

(51) Int. Cl.
*G01N 29/04* (2006.01)
*G01N 29/26* (2006.01)
*G10K 11/26* (2006.01)

(52) U.S. Cl.
CPC .............. *G01N 29/04* (2013.01); *G01N 29/262* (2013.01); *G10K 11/26* (2013.01); *G01N 2291/106* (2013.01)

(58) Field of Classification Search
CPC ................ G01N 29/262; G01N 29/04; G01N 2291/106; G10K 11/26
USPC .......................................................... 73/588
See application file for complete search history.

(56) References Cited

U.S. PATENT DOCUMENTS

| 7,966,860 | B2* | 6/2011 | Dijkstra | 73/1.86 |
| 8,286,488 | B2* | 10/2012 | Meyer et al. | 73/600 |
| 8,783,111 | B2* | 7/2014 | Matsumoto et al. | 73/632 |
| 9,032,802 | B2* | 5/2015 | Imbert et al. | 73/629 |
| 2007/0000328 | A1 | 1/2007 | Buttram | |
| 2013/0047729 | A1 | 2/2013 | Wigh et al. | |
| 2013/0218490 | A1* | 8/2013 | Poirier et al. | 702/56 |

FOREIGN PATENT DOCUMENTS

EP    2124045 A1    11/2009

OTHER PUBLICATIONS

Lamarre et al., "Ultrasound Phased Array Inspection Technology for the Evaluation of Friction Stir Welds", International Symposium on Friction Stir Welding, pp. 1-15, Jun. 26, 2000.
PCT Search Report & Written Opinion issued in connection with corresponding Application No. PCT/US2014031309 on Jul. 2, 2014.

* cited by examiner

*Primary Examiner* — J M Saint Surin
(74) *Attorney, Agent, or Firm* — Cooper Legal Group, LLC

(57) ABSTRACT

A method of selecting one element among a plurality of elements of a phased-array ultrasonic weld inspection arrangement during inspection of a weld to obtain optimum weld inspection coverage. The weld connects portions of material having a known thickness. The elements extend along an ultrasonic transmission wedge of the arrangement that supports the extent of the elements at a wedge angle relative to the welded material. The method includes utilizing material thickness, offset distance of an edge of the wedge from a weld centerline and number of elements within calculation that yields the selection.

9 Claims, 4 Drawing Sheets

AUTOMATIC FIRST ELEMENT SELECTION FOR PHASED ARRAY WELD INSPECTION

BACKGROUND OF THE INVENTION

1. Field of Invention

The present invention relates to ultrasonic inspection of welds, and specifically relates to improved efficiency for completing inspection with an ultrasonic probe having an array of multiple ultrasonic elements.

2. Discussion of Prior Art

Ultrasonic probes are often used to inspect a weld that connects two portions (e.g., sheet members or pipe/conduit sections). Each ultrasonic probe can include a plurality of transducer elements. Each transducer element is capable of emitting a signal that proceeds though the one of the connected portions and into the weld itself. The probe includes a wedge so that the plurality of transducer elements are arranged in an array along the wedge, with each element being at a different location. The difference of location of each transducer element within the array extending along the wedge provides for an associated difference of possible area to which each transducer element will direct its respective signal.

Operation of a probe in order to inspect a weld is often referred to as a scan. In order to perform a scan, the probe is placed upon one of the connected portions at a moderate distance from the weld. The probe is operated (e.g., transducer element signals emitted) and the probe is moved along the connected portion relative to the weld.

In order to accomplish useful inspection of a weld, it is common to perform at least two scans on each side of weld. Specifically, two scans on each side help provide for effective scan coverage of the weld. Both a root of the weld and a cap of the weld should receive effective scanning.

As mentioned, different transducer elements within the array can provide for different area sensing. As such, it is certainly possible that one transducer element can be used to accomplish scanning of the weld root and another transducer element can be used to accomplish scanning of the weld cap. As such, increased efficiency can be obtained via performing the two scans (i.e., one for the weld root and one for the weld cap) generally simultaneously as the probe is moved just once along the each side of the weld. However, because it may not be known which transducer element properly accomplish a scan of the weld root and which element will properly accomplish a scan of the weld cap, it is certainly possible to sequentially operate all of the transducer elements within the array during scan movement along ach side of the weld. Although such a solution is possible, it is easily appreciated that unnecessarily operating all of the transducer elements would result in at least some level of inefficiency. Also, it can be appreciated that even operation of some unnecessarily transducer elements can result in some level of inefficiency. As such, there is a need for improved efficiency. Along these lines there is a need to be able to avoid unnecessarily operating transducer elements and to select/use transducer elements to accomplish the desired scanning.

BRIEF DESCRIPTION OF THE INVENTION

The following summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

In accordance with an aspect, the present invention provides a method of selecting one element among a plurality of elements of a phased-array ultrasonic weld inspection arrangement during inspection of a weld to obtain optimum weld inspection coverage. The weld connects portions of material having a known thickness. The elements extend along an ultrasonic transmission wedge of the arrangement that supports the extent of the elements at a wedge angle relative to the welded material. The method includes utilizing material thickness, offset distance of an edge of the wedge from a weld centerline and number of elements within calculation that yields the selection.

BRIEF DESCRIPTION OF THE DRAWINGS

The foregoing and other aspects of the invention will become apparent to those skilled in the art to which the invention relates upon reading the following description with reference to the accompanying drawings, in which.

DETAILED DESCRIPTION OF THE INVENTION

Figure 1:
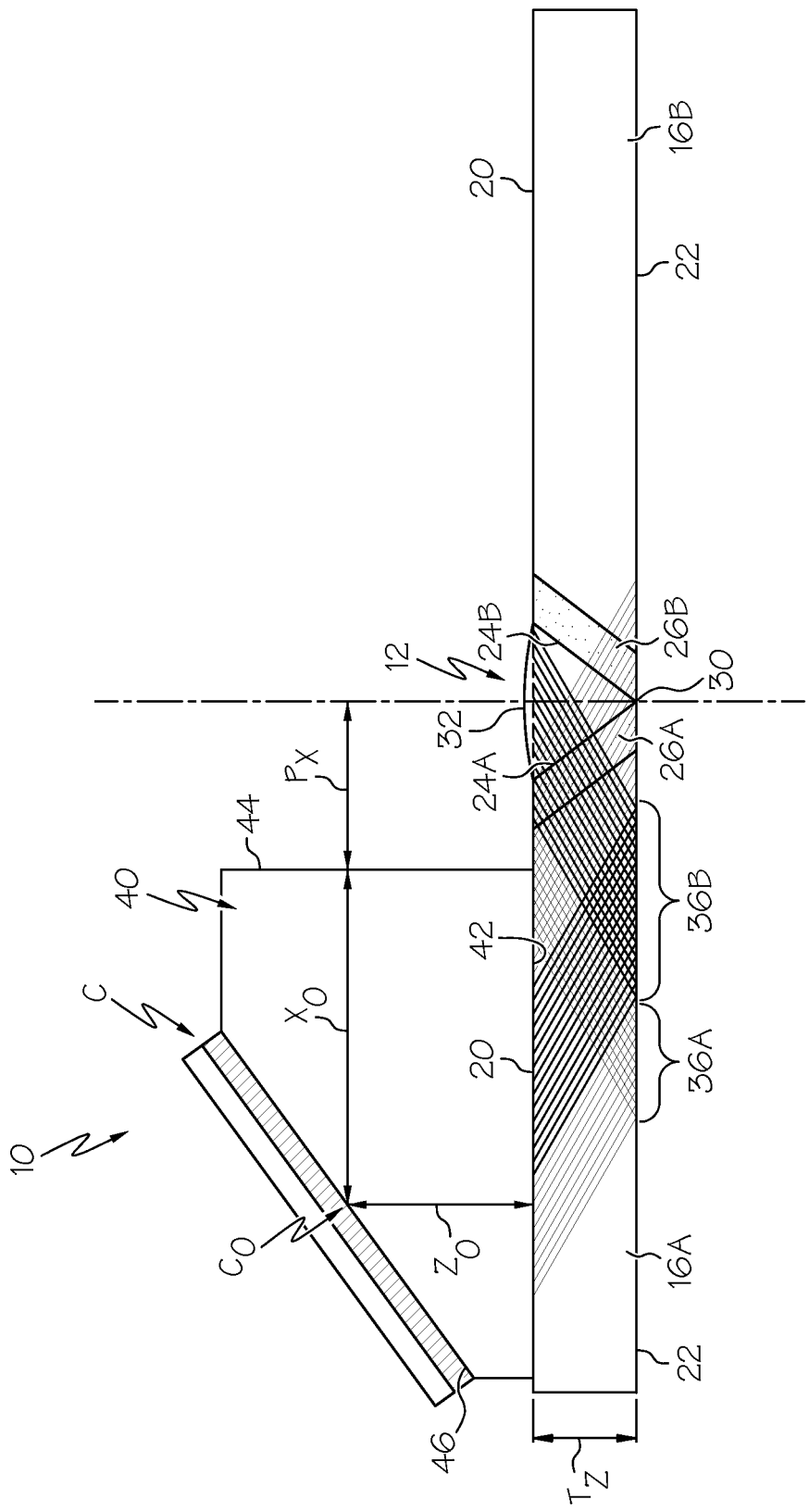
FIG. 1 is a schematic illustration of an ultrasonic probe located upon two portions of material connected by a weld and shows the emittance of signals into a connected portion/weld, with selection of at least one element for selective signal emmitance being able to improve efficiency in accordance with an aspect of the present invention.

Illustrative embodiments that incorporate one or more aspects of the invention are described and illustrated in the drawings. These illustrated examples are not intended to be overall limitations on the invention. For example, one or more aspects of the invention can be utilized in other embodiments. Moreover, certain terminology is used herein for convenience only and is not to be taken as a limitation on the invention. Still further, in the drawings, the same reference numerals are employed for designating the same elements.

An ultrasonic probe 10 is used to inspect an example weld 12 that connects two example portions 16A, 16B of material. It is to be appreciated that the connected portions 16A, 16B need not be a specific limitation upon the present invention. As such, the connected portions can be varied. Some examples of connected portions include sheet members or pipe/conduit sections. The two connected portions 16A, 16B of material can also be varied. Typical examples of the material of the connected portions 16A, 16B include various metals and may include ferrous-based metals, aluminum-based material, or the like. Each connected portion (e.g., 16A, 16)

includes a proximal (e.g., upper as viewed in the Figures) surface 20 and a distal (e.g., lower as viewed in the Figures) surface 22. In the shown example, the two connected portions 16A, 16B, and thus the surfaces 20, 22 are planar. However, it is to be appreciated that some curvature may be present.

The weld 12 that connects the two connected portions 16A, 16B fixes the two portions together and has been previously been completed (i.e., the weld is solidified). The weld 12 may have varied characteristics that need not be specific limitations upon the present invention. For example, the weld 12 may have varied slope and material characteristics concerning composite material(s). The composite materials may be dependent upon the material of the connected portions 16A, 16B. As such, the weld material may include a metal composition, including a ferrous-based or aluminum-based materials or the like.

The weld 12 extends along adjacent edges 24A, 24B of the connected portions 16A, 16B. Within the Figures, the weld 12 extends transverse (e.g., perpendicular) into and out of the plane of the drawing sheet. As such, the Figures show the weld 12 in cross-section. Thus, the weld 12 has a length (i.e., extends perpendicular away from the plane of the drawing sheet) and can be termed to be a weld line. During the creation process (i.e., the welding process) of the example weld 12 shown within the Figures, weld material is deposited. In addition, some of the material 26A, 26B of the connected portions 16A, 16B is altered by the application of heat during the weld creation process. Such altering may include melt or partial melt. As such, the example weld includes a weld root 30 located adjacent to the distal side 22 of the connected portions 16A, 16B and a weld cap 32 located adjacent to the proximal side 20 of the connected portions.

It should be noted that the connected portions 16A, 16B and the weld 12, as they appear within the drawings, are in cross-section. However, it should further be noted that the typical cross-section hatching of the connected portions 16A, 16B and the weld 12 are omitted for clarity since numerous lines representing beams, paths, dimensions, etc. (described below) are shown within the drawings to illustrate aspects of the invention.

It is typical that welds (e.g., weld 12) have an acceptable level of structural integrity and the like. As such, in accordance with one aspect of the present invention, the ultrasonic probe 10 is used to inspect the weld 12. Specifically, in the shown example, the probe 10 is operated during inspection the weld 12 as the probe is moved relative to the weld (i.e., at a spaced distance from the weld line and substantially parallel to the weld line direction). Such operation is often referred to as a scan. In order to perform a scan, the probe 10 is placed upon one (e.g., 16A) of the connected portions 16A, 16B at a moderate distance from the weld 12. The probe 10 is operated and the probe is moved parallel the connected portion relative to the weld 12.

In order to accomplish useful inspection of a weld 12, it is common to perform at least two scans, one on each side of weld 12. Specifically, two scans on the two sides help provide for effective scan coverage of the weld 12.

Turning to the details of the probe 10, the ultrasonic probe includes a plurality of ultrasonic transducer elements C in a linear matrix array. It is to be appreciated that FIG. 1 simply shows an example number of transducer elements C to convey the concept of a plurality of elements C and the shown number is not to be construed as a limitation. In addition, the specific details of the plurality of transducer elements C may be varied. For example, the plurality of transducer elements may be appropriately connected to a power source, connected to data processing components, etc. Also, the physical construction concerning the transducer elements (e.g., extent/spacing of the plurality of transducer elements) can be varied and thus need not be specific limitations upon the present invention.

Each transducer element C is capable of emitting an ultrasonic signal (e.g., an ultrasonic beam) 36 (see example beam in FIG. 3, note that FIG. 3 merely generically shows the transducer elements C) that can proceed though the material of the connected portions 16A, 16B and the material of the weld 12. The signal can be reflected (echoed) back toward the transducer elements of the probe by various surface interfaces and by characteristic of the weld including defects (e.g., imperfections, deformities, voids, impurities, and the like) that provide surface interfaces.

The reflected signals can be analyzed in order to make determinations about the weld. The reflected signal data analysis can be accomplished via various techniques and as such the analysis need not be a specific limitation upon the present invention. Operation of such a probe 10, including the powering/operation of transducer elements C, and processing of signals/data derived from the transducer elements are known and can be varied. In addition, various components/devices can be operatively connected to the probe to receive/process the signals/data derived from the transducer elements to determine various characteristics of the weld including defects (e.g., imperfections, deformities, voids, impurities, and the like). Such components/devices and such reception/processing are known and can be varied. Accordingly, such specifics need not be limitations upon the present invention.

Turning to the specific structure of the example probe 10, the ultrasonic transducer elements C are arranged in a linear matrix array. As a reference, the linear array extends transverse (e.g., perpendicular) to the extent of the weld 12. Recall that the weld 12 extends perpendicular to the plane of the drawing sheet (e.g., into and out from the sheet). As such, the linear array extends within in the plane of the drawing sheet.

The probe 10 includes a wedge 40. The wedge 40 is made of ultrasonic transmissive material. The wedge 40 has a first side 42 for placement against the proximate surface 20 of one of the connected portions (e.g., 16A). As mentioned, the shown example connected portions (16A, 16B) are flat and as such the first side 42 of the wedge 40 has a complementary, substantially flat face to mate against the flat of the connected portion 16A. A different contour of the connected portions can be accommodated via a complementary contour at the first side 42. A second side 44 in the shown example is perpendicular to the first side 42 and is also substantially flat. However it is contemplated that a different configuration is possible. A third side 46 can be referred to as a hypotenuse side and extends at an angle to the first side 42 and thus the flat of the connected portion (e.g., 16A). The hypotenuse side extends at a wedge angle $W_A$ (See FIG. 2). It is contemplated that the hypotenuse side 46 need not extend completely to the first and second sides 42, 44 and the shown example presents truncations so that the hypotenuse side 46 does not extend completely to the first and second sides.

The array of transducer elements C is located on the hypotenuse side 46 of the wedge 40 such that the array extends vertically at an angle up and away from the connected portion (e.g., 16A) as the array laterally extends toward the weld 12. As such, the plurality of transducer elements C are arranged in the array along the wedge 40, with each element being at a different location. The difference of location of each transducer element C within the array extending along the wedge 40 provides for an associated difference of possible area to which each transducer element will direct its respective signal (see, FIG. 1). Specifically, each of the transducer elements C within the array emits a respective signal that enters the wedge at a different location and thus enters the connected portion (e.g., 16A) at a different location. Some example beam groups (e.g., 36A, 36B) from the different transducer elements C within the connected portions 16A, 16B and the weld 12 are shown in FIG. 1. It is to be appreciated that the beams traveling through the wedge 40 are not shown in FIG. 1 for clarity and also some of the overall possible beams may not be shown. See FIG. 3 for an example single beam progressing from a respective transducer element (e.g., C), through the wedge 40 and into the connected portion (e.g., 16A). It should be noted that the plural beams (FIG. 1) within the presented example are directed so at to proceed parallel to each other as they proceed from the array of transducer elements C.

Turning back to the aspect of each beam entering the wedge at a different location and thus entering the connected portion (e.g., 16A) at a different location, such difference provides for different transducer beams to be able to "sense" (e.g., investigate, interrogate, etc.) a different location, including possibly different locations that may or may not contain the weld and may contain different portions of the weld. An ability to effectively and efficiently scan and analyze all portions of the weld (i.e., including the weld root and the weld crown) is beneficial. So logically, different transducer elements and associated different beams can be employed to accomplish this beneficial function. It should also be noted that merely utilizing all transducer elements/beams is somewhat inefficient since some beams will not travel through any portion of the weld and thus do not have an ability to detect/provide information about the weld.

Note that within the example shown within FIG. 1, the first group of transducer element beams 36A proceeds within the connected portion (e.g., 16A) along three legs (with each leg extending between the surfaces 20, 22 and terminating at reflection) and eventually "covers" (e.g., proceeds through) the root 30 of the weld 12. A second group of transducer element beams 36B proceeds within the connected portion (e.g., 16A) along two legs (again with each leg extending between the surfaces 20, 22 and terminating at reflection) and eventually "covers" (e.g., proceeds through) the cap 32 of the weld 12.

As mentioned, different transducer elements within the array C can provide for different area sensing. As such, in accordance with an aspect of the present invention, it possible that one transducer element, or smaller group of transducer elements, can be used to accomplish scanning of the weld root and another transducer element, or smaller group of transducer elements, can be used to accomplish scanning of the weld cap. Accordingly, increased efficiency can be obtained via performing the two scans (i.e., one for the weld root and one for the weld cap) generally simultaneously as the probe is moved just once along the each side of the weld. As another aspect of increased efficiency the other/remaining transducer elements that may not provide for desired scanning can idled or otherwise omitted from operation. However, because it may not be initially known which transducer element(s) will properly accomplish a scan of the weld root and which element(s) will properly accomplish a scan of the weld cap, an aspect of the present invention is to make determinations of such.

Selection of an initial transducer element of the array is provided by a process in accordance with the present invention. In one specific example process an iterative methodology is utilized such that at least some process steps are repeated. One example series of algorithms is provided to do such a process. It is to be appreciated that other algorithms are possible and are to be considered to be within the scope of the present invention.

In general, it is to be appreciated that one example process is presented herein. It is to be appreciated that the process may be varied and that other, different processes can also be utilized. It is to be appreciated that such variations and differences are contemplated to be within the scope of the present invention. As such, the present example is not to be considered a limitation boundary of the present invention. For ease of understanding the following nomenclature is presented. It is to be appreciated that the nomenclature can also be varied without departing from the present invention.

Nomenclature $E_n$=Element number output for each iterative step n, where "n" successively equals 1 to 10

Figure 2:
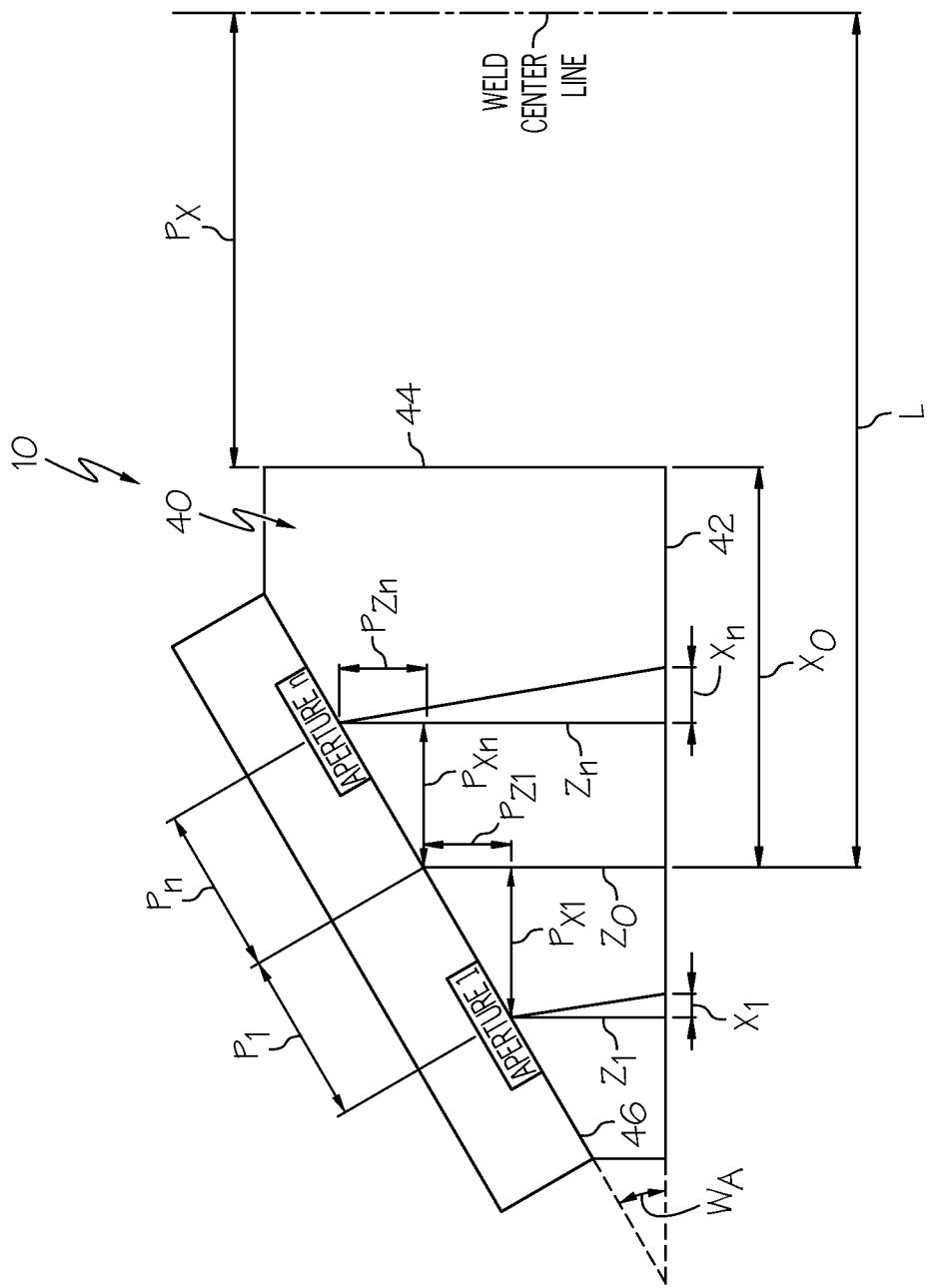
FIG. 2 is a schematic illustration of the ultrasonic probe of FIG. 1 and an schematically shows two element aperture groups, from among a entirety of elements (non-group elements omitted for clarity), and geometric relationships used to optimize operation of transducer elements in accordance with an aspect of the present invention.

$N_0$=Total number of transducer elements within the array of the probe $W_A$=Wedge angle, which is the angle between the upper surface of the connected portion (i.e., the be welded portion) and the array of transducer elements as defined by the wedge interposed there between (shown within FIG. 2)

$C_0$=Probe center element, which is the element that is located within the overall center of the array of the probe Aperture 1=a first subset of elements within the array (shown within FIG. 2)

Aperture n=an $n^{th}$ subset of elements within the array (shown within FIG. 2)

$C_1$=Aperture 1 center element, which is the center element within the group of elements defined as Aperture 1

$C_n$=Aperture n center element, which is the center element within the group of elements defined as Aperture n $Z_0$=Vertical wedge offset, which is the vertical distance of the Probe center element, $C_0$, from the material to be welded as a starting offset value (shown within FIG. 2)

$X_0$=Horizontal wedge offset, which is the horizontal distance of the Probe center element, $C_0$, from the edge of the wedge closest to the weld as a starting offset value (shown within FIG. 2)

$P_1$=Distance, along the array, between the Aperture 1 center element, $C_1$, and the overall center element, $C_0$, of the array (shown within FIG. 2)

$P_n$=Distance along the array between the center element of Aperture 2 and the overall center element of the array (shown within FIG. 2)

$Z_1$=Aperture1 Offset Z, which is the vertical distance from the welded material to the center element $C_1$ of Aperture 1 (shown within FIG. 2)

$Z_n$=Aperture n Offset Z, which is the vertical distance from the welded material to the center element $C_n$ of Aperture n (shown within FIG. 2)

$X_1$=Horizontal distance between Aperture 1 emission point to Beam exit point from Aperture 1 (shown within FIG. 2)

$X_n$=Horizontal distance between Aperture n emission point to Beam exit point from Aperture n (shown within FIG. 2)

$P_{Z1}$=Vertical distance between the probe center element and the Aperture 1 center element (shown within FIG. 2)

$P_{Zn}$=Vertical distance between the probe center element and the Aperture n center element (shown within FIG. 2)

$P_{X1}$=Horizontal distance between the probe center element and the Aperture 1 center element (shown within FIG. 2)

$P_{Xn}$=Horizontal distance between the probe center element and the Aperture n center element (shown within FIG. 2)

$V_W$=Wedge Velocity, which is the known velocity of the ultrasonic beam within the wedge (inputted for use within the iteration process)

$V_S$=Material Velocity, which is the known velocity of the ultrasonic beam within the material of the connected portion (inputted for use within the iteration process)

Figure 3:
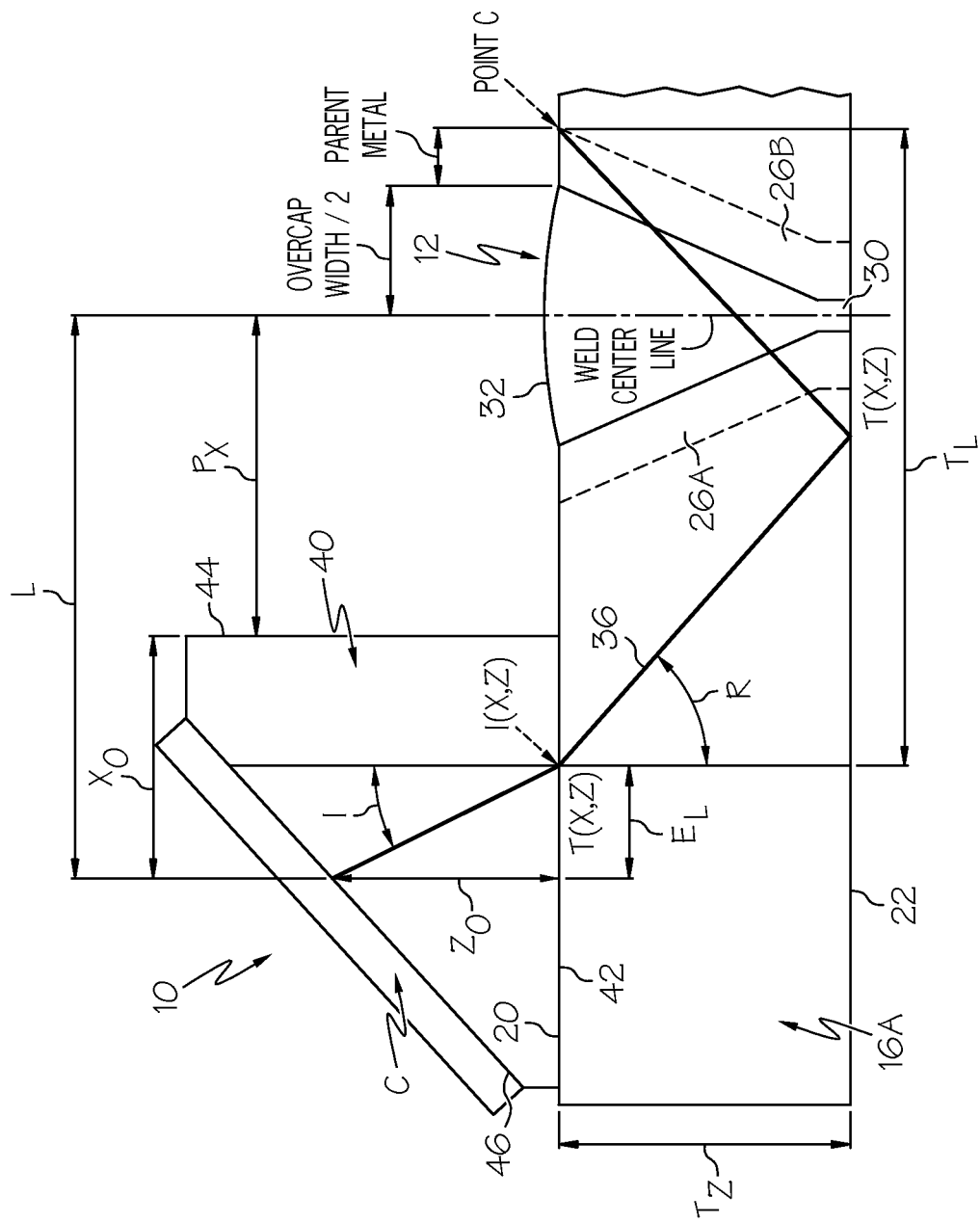
FIG. 3 is a schematic illustration of the ultrasonic probe of FIG. 1 located upon the two portions connected by the weld and shows further geometric relationships used to optimize operation of transducers element in accordance with an aspect of the present invention.

$T_Z$=Material Thickness, which is the vertical thickness of the connected portion that is welded (inputted for use within the iteration process and shown within FIGS. 1 and 3)

$P_X$=Probe Position, which is the horizontal distance between the edge of the wedge closest to the weld and the centerline of the weld (shown within FIGS. 1-3)

L=Horizontal distance of the Probe center element, $C_0$, from the centerline of the weld (shown in FIGS. 2 and 3)

$L_n$=Horizontal distance of the calculated element, n, from the centerline of the weld, wherein n is the $n^{th}$ iteration R=Beam Angle for Linear Scan (shown within FIG. 3)

$T_L$=Distance from the start of beam to end of the beam inside the connected portions Leg=Number of times beam bounce/reflect inside the connected portions I=Incident Angle (shown in FIG. 3)

B=Step Angle

Pitch=Center to center distance between two adjacent probe elements

Overcap width=Horizontal distance of weld top cap (shown within FIG. 3)

Parent metal=Horizontal width of heat affected zone on parent metal. That is heat transferred from molten metal on weld preparation. (shown within FIG. 3)

Using the above nomenclature, the example process is as follows. It is to be appreciated that the example process includes multiple iterations. Within the presented example there are ten iterations. It is to be appreciated that iterations 3 to 9 are not set forth in text and they are easily appreciated via review and understanding of the other iterative steps.

Iterative Steps of the Example Process

Step 1: $E_1=N_0/2$, but if $E_1<1$, set $E_1$ to 1

Step 2: $I=\text{Sin}^{-1}[(\text{Sin}(R))*(V_W/V_S)]$

Step 3: $T_L=\text{Leg}*T_Z*\tan(R)$

Step 4: $E_L=\text{Offset } Z_n*\tan(I)$, where Offset $Z_n=Z_0+[(\text{Pitch}*(E_1-(N_0/2)))*\sin(W_A)]$ Step 5: $L_1=T_L+E_L+P_{Xn}$, where $P_{Xn}=\text{Pitch}*(E_1-(N_0/2))*\text{Cos}(W_A)$ Step 6: $X=P_X+X_0-$(Overcap Width/2)$-$Parent Metal Step 7: $N_1=\text{If}((([(L_1-X)/\text{Cos}(W_A)]/\text{Pitch}]/2) \geq N_0), N_0, ((([(L_1-X)/\text{Cos}(W_A)]/\text{Pitch}]/2)$    Iteration 1

Step 1: $E_2=\text{If}((E_1+N_1)\geq N_0, N_0, (E_1+N_1))$, but if ($E_2<1$, set $E_2$ to 1)

Step 2: $B=\text{Sin}^{-1}[(\text{Sin}(R))*(V_W/V_S)]$

Step 3: $T_L=\text{Leg}*T_Z*\tan(R)$

Step 4: $E_L=\text{Offset } Zn*\tan(B)$, where Offset $Z_n=Z_0+[(\text{Pitch}*(E_2-(N_0/2)))*\sin(W_A)]$ Step 5: $L_2=T_L+E_L+P_{xn}$, where $P_{Xn}=\text{Pitch}*(E_2-(N_0/2))*\text{Cos}(W_A)$ Step 6: $X=P_X+X_0-$(Overcap Width/2)$-$Parent Metal Step 7: $N_2=\text{If}((([(L_2-X)/\text{Cos}(W_A)]/\text{Pitch}]/2)\geq N_0), N_0, ((([(L_2-X)/\text{Cos}(W_A)]/\text{Pitch}]/2)$    Iteration 2

Similar steps are performed for iterations 3 to 9.

Step 1: $E_{10}=\text{If}((E_9+N9_9)\geq N_0, N_0, (E_9+N_9))$, but if ($E_{10}<1$, set $E_{10}$ to 1)

Step 2: $B=\text{Sin}^{-1}[(\text{Sin}(R))*(V_W/V_S)]$

Step 3: $T_L=\text{Leg}*T_Z*\tan(R)$

Step 4: $E_L=\text{Offset } Zn*\tan(B)$, where Offset $Z_n=Z_0+[(\text{Pitch}*(E_{10}-(N_0/2)))*\sin(W_A)]$ Step 5: $L_{10}=T_L+E_L+P_{xn}$, where $P_{Xn}=\text{Pitch}*(E_{10}-(N_0/2))*\text{Cos}(W_A)$ Step 6: $X=$Probe Position+Wedge Offset $X-$(Overcap Width/2)$-$Parent Metal Step 7: $N_{10}=\text{If}((([(L_{10}-X)/\text{Cos}(W_A)]/\text{Pitch}]/2)\geq N_0), N_0, ((([(L_{10}-X)/\text{Cos}(W_A)]/\text{Pitch}]/2)$    Iteration 10

Within the presented example, the iteration has to be computed ten times to determine the optimal first element, which hits the targeted location. Once the optimal first element is determined, the scan can occur in an efficient manner. For example, as presented, some certain elements can be idled (e.g., not operated) and/or data from such some certain elements can be ignored and or otherwise not involved in processing/analysis.

It is to be appreciated that the process in accordance with to the present can be performed via the aid of a calculation device and/or a computer. Of course, in a most basic form, the process can be performed without the aid of such devices. However, use of such devices would itself provide for improved efficiency.

Figure 4:
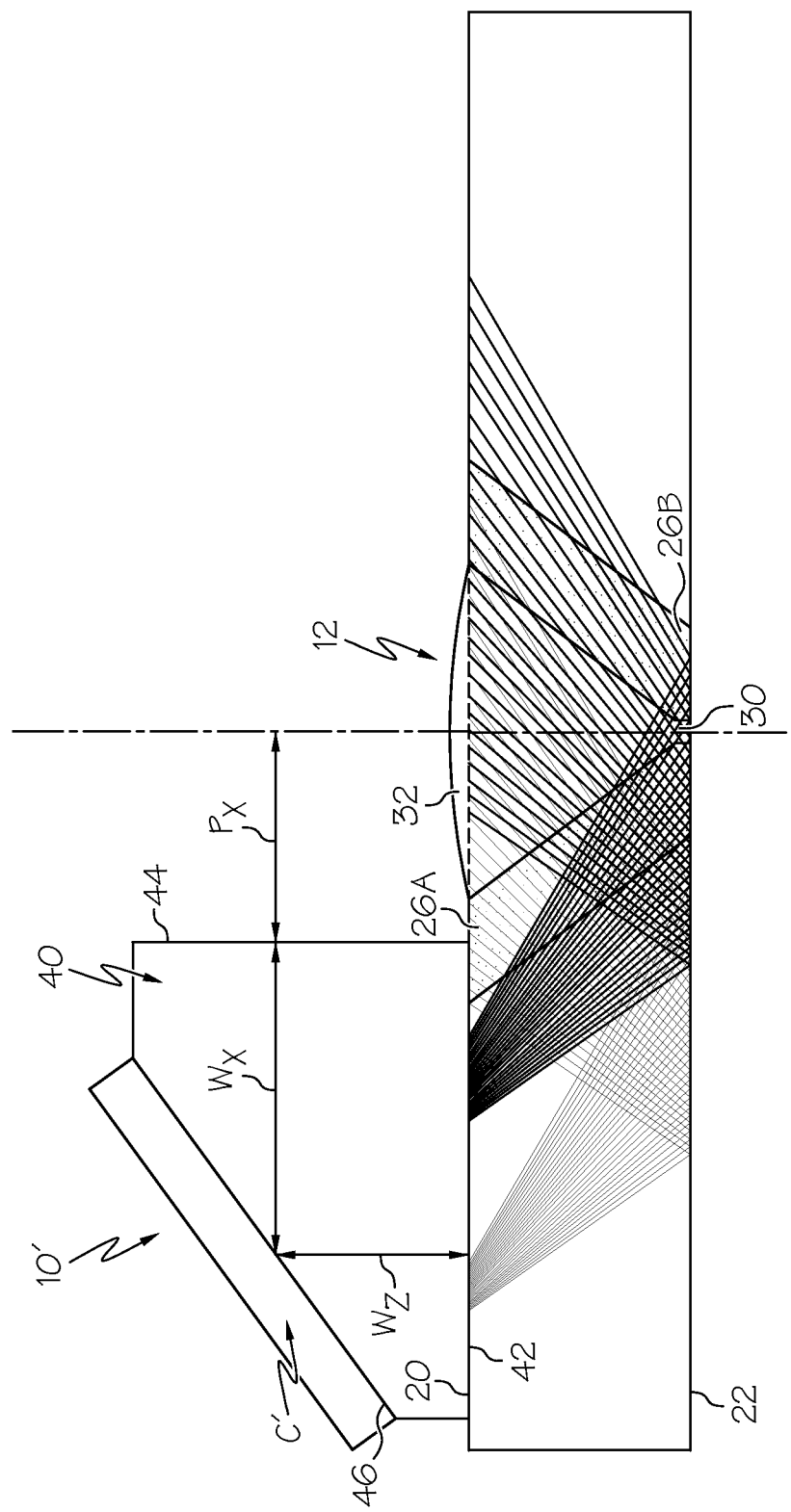
FIG. 4 is a schematic illustration of another ultrasonic probe located upon two portions connected by a weld similar to FIG. 1 and shows the emittance of signals into a connected portion/weld that can be optimized in accordance with an aspect of the present invention.

It is to be appreciated that the present invention may be utilized with other types of ultrasonic probes. One specific example of another type of probe with which the present invention may be utilized is a sector scan type probe 10' (FIG. 4). The sector scan type probe 10' provides for a divergence of beam from each of its plurality of transducer elements C'. Again the iterative process may be used, but the beam angle, due to divergence, is simply factored into the iteration to again determine an initial transducer element.

An example of the invention has been described with reference to the example embodiments described above. Modifications and alterations will occur to others upon a reading and understanding of this specification. Example embodiments incorporating one or more aspects of the invention are intended to include all such modifications and alterations insofar as they come within the scope of the appended claims.

What is claimed:

1. A method of selecting one element among a plurality of elements of a phased-array ultrasonic weld inspection arrangement during inspection of a weld connecting portions of material having a known thickness to obtain optimum weld inspection coverage, wherein the elements extend along an ultrasonic transmission wedge of the arrangement that supports the extent of the elements at a wedge angle relative to the welded material; the method including:

utilizing material thickness, offset distance of an edge of the wedge from a weld centerline and number of elements within calculation that yields the selection.

2. A method as set forth within claim 1, wherein the calculation includes iterations of successive calculation steps.

3. A method as set forth within claim 1, wherein the wherein the calculation includes utilizing the velocity of ultrasound beams from the elements within the connected portions and the velocity of ultrasound beams from the elements within the wedge.

4. A method as set forth within claim 1, wherein the beams can travel within the connection portions along legs between reflections, and the calculation includes utilizing the number of legs between reflections.

5. A method as set forth within claim 1, wherein the wherein the calculation includes utilizing a vertical distance between a probe center element and a surface of the connected portion.

6. A method as set forth within claim 1, wherein the wherein the calculation includes utilizing a horizontal distance between a probe center element and a front surface of the wedge that is nearest to the weld.

7. A method as set forth within claim 1, wherein the elements extend along the wedge of the arrangement that supports the extent of the elements at a wedge angle relative to the welded material, and the method includes utilizing the wedge angle within the calculation that yields the selection of the at least one element.

8. A method as set forth within claim 1, wherein the calculation includes utilizing the dimension of a cap of the weld.

9. A method as set forth within claim 1, wherein the method is utilized with an inspection arrangement that has an array of linear scan elements.

* * * * *